United States Patent
Kwon et al.

(10) Patent No.: US 9,682,030 B2
(45) Date of Patent: Jun. 20, 2017

(54) METHOD FOR PREPARING POLYSACCHARIDE OF GREEN TEA AND COSMETIC COMPOSITION FOR SKIN WHITENING, MOISTURIZATION AND ANTI-WRINKLE EFFECTS COMPRISING THE POLYSACCHARIDE

(71) Applicant: AMOREPACIFIC CORPORATION, Seoul (KR)

(72) Inventors: Sun Sang Kwon, Gyeonggi-do (KR); Myeong Hun Yeom, Gyeonggi-do (KR); Duck Hee Kim, Seoul (KR); Han Kon Kim, Gyeonggi-do (KR); Nok Hyun Park, Gyeonggi-do (KR); Soo Mi Ahn, Gyeonggi-do (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 14/450,349

(22) Filed: Aug. 4, 2014

(65) Prior Publication Data

US 2014/0341827 A1 Nov. 20, 2014

Related U.S. Application Data

(62) Division of application No. 13/055,262, filed as application No. PCT/KR2009/002365 on May 6, 2009, now Pat. No. 8,835,404.

(30) Foreign Application Priority Data

Jul. 22, 2008 (KR) .................. 10-2008-0070987

(51) Int. Cl.
| | | |
|---|---|---|
| *A61K 8/73* | (2006.01) | |
| *A61K 8/97* | (2017.01) | |
| *A61Q 19/00* | (2006.01) | |
| *A61Q 19/02* | (2006.01) | |
| *A61Q 19/08* | (2006.01) | |

(52) U.S. Cl.
CPC .............. *A61K 8/73* (2013.01); *A61K 8/97* (2013.01); *A61Q 19/007* (2013.01); *A61Q 19/02* (2013.01); *A61Q 19/08* (2013.01); *A61K 2800/74* (2013.01); *A61K 2800/782* (2013.01)

(58) Field of Classification Search
None
See application file for complete search history.

(56) References Cited

U.S. PATENT DOCUMENTS

| 2004/0146539 A1 | 7/2004 | Gupta |
| 2008/0113044 A1 | 5/2008 | Alberte et al. |
| 2014/0341827 A1† | 11/2014 | Kwon et al. |

FOREIGN PATENT DOCUMENTS

| JP | 2009-143849 | 7/2009 |
| KR | 10-0700912 | 3/2007 |
| WO | WO 2007/109802 | 9/2007 |

OTHER PUBLICATIONS

International Search Report for PCT/KR2009/002365, mailed Dec. 17, 2009.
Written Opinion for PCT/KR2009/002365, mailed Dec. 17, 2009.
Lee et al, "Inhibition of Pathogenic Bacterial Adhesion by Acidic Polysaccharide from Green Tea (*Camellia sinensis*)", Journal of Agricultural and Food Chemistry 2006, 54, 8717-8723.
Aoki et al, "Melanogenesis Inhibition by an Oolong Tea Extract in B16 Mouse Melanoma Cells and UV-Induced Skin Pigmentation in Brownish Guinea Pigs", Biosci. Biotechnol. Biochem., 71 (8), 1879-1885, 2007.
Youn et al, "Evaluation of the Anti-Inflammatory Effect of a Moisturizer Containing Green-Tea Extracts", Korean Journal of Dermatology, 2003, vol. 41, No. 1, pp. 15-20.
Chen et al, "Antioxidant activities of different fractions of polysaccharide conjugates from green tea (*Camellia sinensis*)", Food Chemistry 106 (2008) 559-563.
Monobe et al, "Immunostimulating activity of a crude polysaccharide derived from green tea (*Camellia sinensis*) extract", Journal of Agricultural Food and Chemistry, Jan. 31, 2008, vol. 56, pp. 1423-1427.
Wei et al, "Protective effects of Tea Polysaccharides and Polyphenol on Skin", Journal of Agricultural and Food Chemistry, Nov. 8, 2009, vol. 571, pp. 7757-7762.
Hashizume, The Journal of Dermatology vol. 31: 603-669, 2004.
Trommer et al, International Journal of Pharmaceutics 298 (2005) 153-163.
Chen et al Food Chemistry 106 (Jan. 2008) 559-563.
Mohammad Najmul Ghani Khan, Khazaain-al-Advia, vol. II, p. 6 (p. 03-08), ( Ref.p. of publication:342-343 ), 1911 AD, Nadeem Yunus Printer / Sheikh Mohd Basheer & Sons, Lahore.†

† cited by third party

*Primary Examiner* — Layla Berry
(74) *Attorney, Agent, or Firm* — Nixon & Vanderhye P.C.

(57) ABSTRACT

Disclosed is a method for preparing polysaccharides of green tea, and more particularly to a method for preparing polysaccharides of green tea comprising the steps of: a) removing chlorophyll and a low molecular weight polyphenol from green tea powder using a solvent; b) hot-water extracting a water-soluble active ingredient from the green tea residue of step a); and c) separating the polysaccharides of green tea from the hot-water extract of step b) by ultrafiltration and ethanol precipitation. Also, the present invention relates to a cosmetic composition for skin whitening, moisturization and anti-wrinkle effects comprising the polysaccharides of green tea as an effective ingredient.

10 Claims, 2 Drawing Sheets

METHOD FOR PREPARING POLYSACCHARIDE OF GREEN TEA AND COSMETIC COMPOSITION FOR SKIN WHITENING, MOISTURIZATION AND ANTI-WRINKLE EFFECTS COMPRISING THE POLYSACCHARIDE

This application is a divisional of application Ser. No. 13/055,262 filed Jan. 21, 2011, now allowed, which in turn is the U.S. national phase of International Application No. PCT/KR2009/002365 filed 6 May 2009 which designated the U.S. and claims priority to KR Patent Application No. 10-2008-0070987 filed 22 Jul. 2008, the entire contents of each of which are hereby incorporated by reference.

TECHNICAL FIELD

The present invention relates to a method for preparing polysaccharides of green tea, and more particularly to a method for preparing polysaccharides of green tea comprising the steps of:
 a) removing chlorophyll and low molecular weight polyphenols from green tea powder using a solvent;
 b) hot-water extracting water-soluble active ingredients from the green tea residue of step a); and
 c) separating the polysaccharides of green tea from the hot-water extract of step b) by ultrafiltration and ethanol precipitation. Also, the present invention relates to a cosmetic composition for skin whitening, moisturization and anti-wrinkle effects comprising the polysaccharides of green tea as an effective ingredient.

BACKGROUND ART

Green tea contains many active ingredients of benefit to humans. These active ingredients include catechins such as epicatechin, epigallocatechin, epicatechingallate and epigallocatechingallate, which are known for anti-tumor effect, anti-oxidizing effect, anti-bacterial effect, detoxication of heavy metals and suppression of high blood pressure.

Nowadays, studies are being actively conducted to search for pharmacological active substances in the green tea other than the catechins. Polyphenols extracted from the green tea are reported to have an inhibitory effect on photo-aging and can be used as a UV protecting agent. Also, gallocatechingallate as an isomer is studied for its extraction. Further, dermal formulations for external application comprising the green tea extract are studied for improvement of wrinkling and elasticity deterioration caused by skin aging. This is because the polyphenols contained in the green tea can eliminate free radicals and activate defense factors that are related to the anti-oxidation in the skin, and thereby, improve wrinkling and skin elasticity.

In addition, water soluble polysaccharides existing in the green tea are known to have immunization, anti-radioactivity, anti-coagulant, anti-tumor, anti-HIV and reduction of blood glucose level activities. The polysaccharides isolated and purified from the green tea have an activity to suppress the bonding between *Propionibacterium acne* and atopic *Staphylococcus aureus* and the bonding between *Helicobacter pylori* and host cells in the human body. In cited references, ion exchange and gel filtration chromatography are used to separate the polysaccharides of the green tea. However, the ion exchange and gel filtration chromatography processes are inferior in terms of economical efficiency since they require excessive time, and no techniques for mass production have yet been established.

Thus, the green tea extract cannot avoid the necessity of being used in combination with other effective ingredients, since it has poor formulation stability such as discoloration and cannot be used in a large amount to be capable of providing desired effects such as whitening, moisturizing and anti-wrinkle effects despite having various active substances.

Also, polyphenols which are representative ingredients of the green tea and known to have anti-oxidizing effect must be secondarily processed, for example, into a capsule form, since they have poor formulation stability and stability as they are. However, even when formulated into the capsule form, the polyphenols can be readily discolored over time and thus cannot be used as cosmetic materials.

DISCLOSURE

Technical Problem

Accordingly, the present inventors have conducted studies to seek a method for preparing polysaccharides of green tea in a more economical way, and as a result, have developed a method for preparing polysaccharides of green tea comprising the steps of:
 a) removing chlorophyll and low molecular weight polyphenols from green tea powder using a solvent;
 b) hot-water extracting water-soluble active ingredients from the green tea residue of step a); and
 c) separating the polysaccharides of green tea from the hot-water extract of step b) by ultrafiltration and ethanol precipitation. By this method, it is possible to prepare the polysaccharides of green tea in a short process time and in large quantities, leading to an increase in economical efficiency. Based on this finding, the present invention has been completed.

Also, the inventors have found that a cosmetic composition comprising the polysaccharides of green tea shows excellent skin whitening, skin moisturizing and anti-wrinkle effects.

Therefore, an object of the present invention is to provide a method for preparing polysaccharides of green tea at a high economical efficiency.

Further, another object of the present invention is to provide a cosmetic composition for skin whitening, skin moisturizing and anti-wrinkle effects.

Technical Solution

To achieve the above object, the present invention provides a method for preparing polysaccharides of green tea comprising the steps of:
 a) removing chlorophyll and low molecular weight polyphenols from green tea powder using a solvent;
 b) hot-water extracting water-soluble active ingredients from the green tea residue of step a); and
 c) separating the polysaccharides of green tea from the hot-water extract of step b) by ultrafiltration and ethanol precipitation.

In another aspect, the present invention provides a cosmetic composition for skin whitening, moisturization and anti-wrinkle effects comprising the polysaccharides of green tea as an effective ingredient.

Advantageous Effects

When polysaccharides of green tea are prepared by the method according to the present invention, it is possible to reduce the production time and to produce the polysaccharides of green tea in large quantities, leading to an improvement in economical efficiency. Also, the cosmetic composition comprising the polysaccharides of green tea as an effective ingredient according to the present invention can provide excellent skin whitening, moisturizing and anti-wrinkle effects without skin irritation.

BEST MODE

Figure 1:
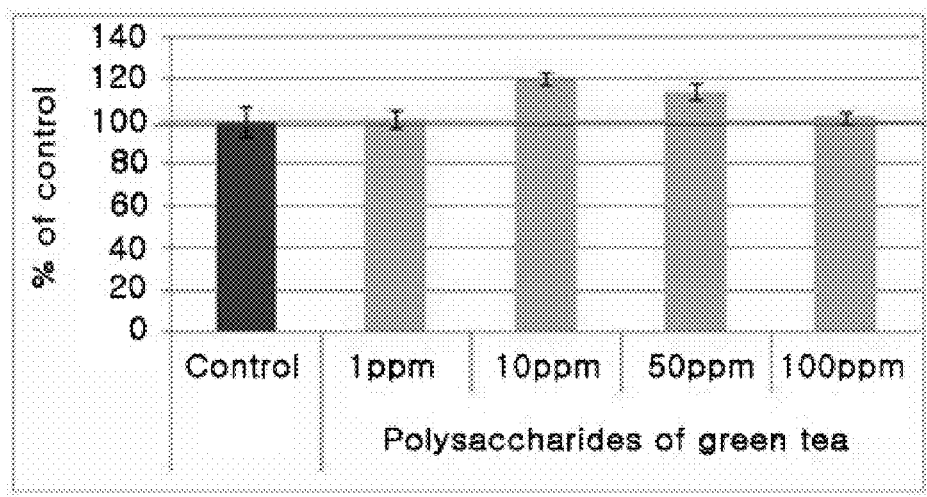
FIG. 1 is a graph showing the result of a cytotoxicity test of the polysaccharides of green tea.

The present invention relates to a method for preparing polysaccharides of green tea, and more particularly to a method for preparing polysaccharides of green tea comprising the steps of:

a) removing chlorophyll and low molecular weight polyphenols from green tea powder using a solvent;

b) hot-water extracting water-soluble active ingredients from the green tea residue of step a); and c) separating the polysaccharides of green tea from the hot-water extract of step b) by ultrafiltration and ethanol precipitation.

Also, the present invention relates to a cosmetic composition for skin whitening, moisturization and anti-wrinkle effects comprising the polysaccharides of green tea as an effective ingredient.

Hereinafters, the present invention is described in detail.

The polysaccharides of green tea according to the present invention are derived from *camellia sinensis*, a member of tea trees belonging to the family Theaceae and the genus *Camellia*, which is an evergreen shrub known to have immunization, anti-radioactivity, anti-coagulant, anti-tumor, anti-HIV and reduction of blood glucose level activities. Also, the polysaccharides of green tea suppress generation of melanin and expression of matrix metalloprotease-1 (MMP-1) and increase skin moisturization, without cytotoxicity, which leads to skin irritation, whereby it can show skin whitening, skin moisturizing and anti-wrinkle effects.

The individual steps of the method for preparing polysaccharides of green tea according to the present invention are described in detail below.

Step a) to remove chlorophyll and low molecular weight polyphenols from the green tea powder using a solvent:

In order to remove chlorophyll and low molecular weight polyphenols from the green tea powder, solvent extraction is performed. The extraction solvent is preferably at least one selected from the group consisting of hexane, ethanol and methanol. In order to prevent toxicity that may be caused by the residue upon application to cosmetics, ethanol is more preferably used.

The solvent is added to the green tea powder and thoroughly stirred at room temperature. The solvent in which chlorophyll and low molecular weight polyphenols are dissolved is then removed by centrifugation. The resulting residue is dried to obtain a product containing no chlorophyll and low molecular weight polyphenols.

Step b) to hot-water extract water-soluble active ingredients from the residue of step a):

In order to extract water-soluble active ingredients from the residue prepared in step a), hot-water extraction is performed. The hot-water extraction is performed preferably at a temperature of 30 to 40° C. This is because if the temperature exceeds 40° C., thermal denaturation can occur, while if the temperature is lower than 30° C., the polysaccharides are not sufficiently extracted. Also, the hot-water extraction is performed preferably for 6 to 8 hours. This is because if the time exceeds 8 hours, contamination by microorganisms can occur, while if the time is less than 6 hours, the polysaccharides are not sufficiently extracted. The extract obtained from the hot-water extraction is filtered using a filtering apparatus and concentrated in vacuo.

Step c) to separate polysaccharides of green tea from the hot-water extract of step b) by ultrafiltration and ethanol precipitation:

In order to separate polysaccharides from the hot-water extract of step b), ultrafiltration and ethanol precipitation is performed. The polysaccharides comprise about 60 to 65% of a polysaccharide part and about 8 to 9% of a protein part. These two parts are connected by amino acid-sugar bond and the rest comprises protein isolates. Therefore, the polysaccharides have molecular weights of 100,000 to 300,000 daltons, which are much greater than those of the protein isolates. By means of this molecular weight difference, the ultrafiltration is performed to separate the polysaccharides of green tea. Also, the ultrafiltration has merits in that it is a continuous process capable of simultaneously performing separation of low molecular weight substances and concentration of the filtrate and in which thermal denaturation does not occur, since the process is practiced at room temperature.

Then, ethanol is slowly added to the ultrafiltration concentrate to perform the ethanol precipitation. Here, ethanol is added preferably at a rate of 100 to 200 ml/min. If ethanol is added at a rate faster than 200 ml/min, the final product particles are too big and bulk up. After completion of the ethanol precipitation, ethanol is removed and the product is dried in vacuo at a temperature of 40 to 50° C. to obtain the polysaccharides of green tea in the powder form.

The polysaccharides of green tea according to the present invention show excellent thermal stability, pH stability and body stability as well as formulation stability. Also, according to the present invention, it is possible to prepare the polysaccharides of green tea at a relatively high yield.

Since the polysaccharides of green tea according to the present invention do not contain ingredients such as polyphenols, which are a main cause of discoloration, unlike the conventional green tea extract, which is limited in its use due to the problems of discoloration, they can be used in a large amount in formulations. Therefore, the cosmetic composition comprising the polysaccharides of green tea can have maximized skin whitening, moisturizing and anti-wrinkle effects without additional effective ingredients.

Therefore, the cosmetic composition according to the present invention comprises the polysaccharides of green tea as an effective ingredient and shows excellent skin whitening, moisturizing and anti-wrinkle effects. The cosmetic composition is not particularly limited in its formulation and can be formulated into skin softener, lotion, moisturizing lotion, massage cream, pack, gel, body lotion, body oil and body essence. Each formulation of the cosmetic composition may include other ingredients than the polysaccharides of green tea according to the formulation type and final use, and the additional ingredients can be properly selected by those skilled in the art without difficulty.

Further, the cosmetic composition comprises the polysaccharides of green tea preferably in an amount of 0.1 to 20% by weight based on the total weight of the composition. If the polysaccharides of green tea are contained in an amount of more than 20% by weight, the formulation stabilization such as phase separation can be affected. If the polysaccharides of green ten are contained in an amount of less than 0.1% by weight, the effects of the formulation are limited.

Hereinafter, the present invention is described in further detail with reference to examples. It should be understood, however, that these examples are for illustrative purposes only and are not to be construed to limit the scope of the present invention.

EXAMPLES

Example 1

Preparation of Polysaccharide of Green Tea

Dried green tea leaves were pulverized and sieved through a screen to obtain green tea powder (d50=100~1000 μm). 10 kg of the green tea powder was dispersed in 150 l of 95% (v/v) ethanol and stirred at room temperature. The mixture was centrifuged to remove chlorophyll and low molecular weight polyphenols. The residue was extracted once with the same solvent and dried.

The product of the extraction, from which the chlorophyll and low molecular weight polyphenols had been removed, was added to 125 l of water and stirred at 35° C. for 7 hours for hot-water extraction. The resulting extract of the polysaccharide of green tea was filtered through a filter press, collected and concentrated in vacuo at 62° C. to 1/10 of the initial volume.

The concentrate of the polysaccharides of green tea was ultrafiltered (molecular weight CUT OFF: 30,000 daltons) to remove low molecular weight protein isolates, and then subjected to the ethanol precipitation by slowly adding ethanol in an amount of 5 times of the final ultrafiltrate at a rate of 100 ml/min. The precipitated polysaccharides of green tea were dried in vacuo at 45° C. to obtain 250 g of the polysaccharides of green tea as powder.

Experimental Example 1

Cytotoxicity Test

Human keratinocyte HaCaT cells were seeded in a 96-well plate, each well containing $1 \times 10^4$ cells, and cultured for 24 hours. The plate was washed once with 100 μl of PBS (phosphate buffered saline), exchanged with media containing 1, 10, 50 and 100 ppm of the polysaccharides of green tea, and cultured for 48 hours. WST-1 solution (Roche Diagnostic GmbH., Germany), diluted 10 times, was added to each well. The plate was incubated at 37° C. for 2 hours. Subsequently, the absorption at 450 nm of the resulting solution was measured. A control group used dimethyl sulfoxide to dissolve the sample. The data of the adsorption were corrected for the data of the control group and the result is shown in FIG. 1.

As shown in FIG. 1, it was noted that the samples containing the polysaccharides of green tea according to the present invention showed cell viabilities similar to the control group and did not have cytotoxicity or induce skin irritation in the used concentration range.

Experimental Example 2

Inhibitory Effect on Melanin Formation

In order to compare the inhibitory effect of the acidic polysaccharides of green tea on melanin formation in cells, this example was performed using arbutin, which is known as a melanin biosynthesis inhibitor, as a comparator. Melanin A cells were seeded into a 24-well plate, each well containing $3 \times 10^4$ cells. One day later, the wells of the plate were treated three times with either 10, 50 and 100 ppm of arbutin or with 1, 10, 50 and 100 ppm of the polysaccharides of green tea. After incubation at 37° C. for 3 days, the wells of the plate were again treated with arbutin or the polysaccharides of green tea by the same method as described above. After incubation for a further 3 days, the plate was washed with PBS. 1N NaOH solution was used to dissolve the formed melanin, and subsequently the absorption at 405 nm of the resulting solution was measured. The control group used dimethyl sulfoxide to dissolve the sample. The data of the absorption were corrected for the data of the control group and the result is shown in FIG. 2.

Figure 2:
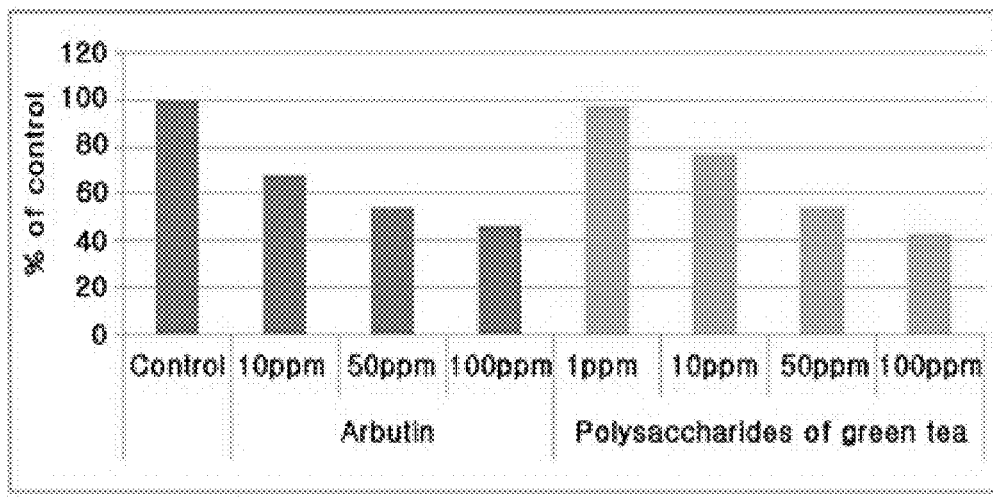
FIG. 2 is a graph showing the inhibitory effect of the polysaccharides of green tea on production of melanin.

As shown in FIG. 2, it was noted that the samples containing the polysaccharides of green tea according to the present invention inhibited the melanin synthesis in proportion to the concentration and that the polysaccharides of green tea have an IC50 of 50 ppm. Therefore, the polysaccharides of green tea according to the present invention showed an inhibitory effect on melanin synthesis similar to that of arbutin. The IC50 was determined as a concentration at which the absorption was reduced to 50%.

Experimental Example 3

Inhibitory Effect on Expression of MMP-1 by UV

In order to confirm the inhibitory effect on expression of matrix MMP-1 increased by exposure to UV, fibroblasts (p6) were seeded in a 12-well plate, each well containing $0.75 \times 10^5$ cells, and starved in serum-free medium for 24 hours. The starved cells were washed with PBS and irradiated by UV (40 mJ). Then, the cells were injected twice with either 10 μM retinoic acid (RA), or with 1, 10 and 50 ppm of the polysaccharides of green tea during a 48 hours period. The isolated MMP-1 in the medium was measured using a kit (Amersham, RPN2610). The data were corrected for the data of a non-UV irradiated control group and the result is shown in FIG. 3.

Figure 3:
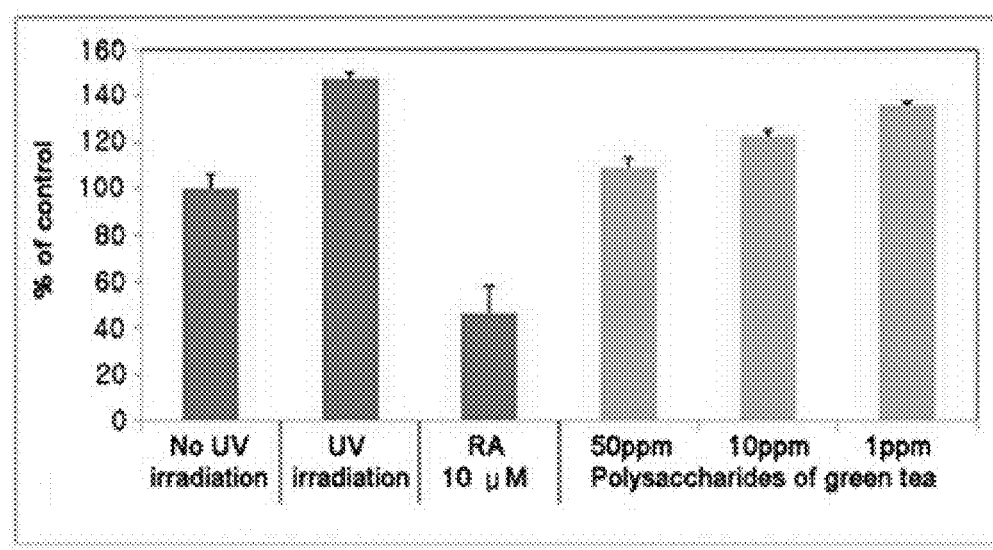
FIG. 3 is a graph showing the inhibitory effect of the polysaccharides of green tea on development of matrix metalloprotease-1 (MMP-1).

As shown in FIG. 3, it was noted that the samples containing the polysaccharides of green tea according to the present invention inhibited the expression of MMP-1 in proportion to the concentration. Particularly, at the concentration of 50 ppm, the polysaccharides of green tea inhibited the expression of MMP-1 at a level similar to the control group that was not irradiated by UV.

Formulation Example 1 and Comparative Example 1: Preparation of Lotion

Formulation Example 1 and Comparative Example 1 were prepared according to the composition described in Table 1 by following the conventional method (unit: % by weight).

TABLE 1

| Ingredients | Formulation Example 1 | Comparative Example 1 |
|---|---|---|
| Purified water | To 100 | To 100 |
| Polysaccharides of green tea of Example 1 | 0.5 | — |
| Bees wax | 4.0 | 4.0 |
| Polysorbate 60 | 1.5 | 1.5 |
| Sorbitan sesquioleate | 1.5 | 1.5 |
| Liquid paraffin | 0.5 | 0.5 |

TABLE 1-continued

| Ingredients | Formulation Example 1 | Comparative Example 1 |
|---|---|---|
| Montana 202 (Seppic) | 5.0 | 5.0 |
| Glycerin | 3.0 | 3.0 |
| Butylene glycol | 3.0 | 3.0 |
| Propylene glycol | 3.0 | 3.0 |
| Carboxyvinyl polymer | 0.1 | 0.1 |
| Triethanol amine | 0.2 | 0.2 |

Experimental Example 4

Increase of Skin Moisturizing Effect on Human Skin 50 male and female adults, 50 to 60 years old, with Xerosis cutis were divided into two groups and given the lotions prepared in Formula Example 1 or Comparative Example 1. The lotion was applied on the face twice a day for 4 weeks. Before the application, the skin's moisture level was measured as a reference using a corneometer in a controlled condition of a constant temperature of 24° C. and a relative humidity of 40%. 1, 2 and 4 weeks after the application was initiated, and 2 weeks after the application was suspended, the skin's moisture level was measured. The result is shown in Table 2. The data show the increase of the skin's moisture level after the application for the predetermined period of time on the basis of the value measured by the corneometer before the experiment.

TABLE 2

| | Increase of skin's moisture level (%) | | | |
|---|---|---|---|---|
| Test material | After 1 week | After 2 weeks | After 4 weeks | 2 weeks after suspension of application |
| Formulation Example 1 | 32 | 42 | 45 | 39 |
| Comparative Example 1 | 29 | 33 | 34 | 15 |

As shown in Table 2, Formulation Example 1 containing the polysaccharides of green tea according to the present invention showed a greater increase rate than Comparative Example 1 not containing the polysaccharides of green tea. Further, even 2 weeks after the application was suspended (total 6 weeks passed), Formulation Example 1 maintained the skin's moisture level similar to those at 1 to 2 weeks after the application was initiated, which indicates that Formulation Example 1 can maintain the skin's moisture level for a certain period of time even after the application is suspended.

The invention claimed is:

1. A cosmetic composition comprising the polysaccharides of green tea as an effective ingredient, wherein the polysaccharides of green tea are characterized in that having a molecular weight of 100,000 to 300,000 daltons, with no having low molecular weight free proteins of below 30,000 Daltons and chlorophyll,
   wherein the polysaccharides of green tea are prepared by the method comprising the following steps of:
   a) removing chlorophyll and low molecular weight polyphenols from green tea powder using a solvent;
   b) hot-water extracting water-soluble active ingredients from the green tea residue of step a) at a temperature of 30 to 40° C. for 6 to 8 hours; and
   c) separating the polysaccharides of green tea removing low molecular weight free proteins from the hot-water extract of step b) by ultrafiltration and then separating the polysaccharides of green tea by ethanol precipitation wherein the polysaccharides of green tea have a molecular weight of 100,000 to 300,000 daltons.

2. The cosmetic of claim 1, wherein the solvent used in step a) is at least one selected from the group consisting of hexane, ethanol and methanol.

3. The composition of claim 1, wherein the molecular weight cut-off of the ultrafiltration is 30,000 Daltons.

4. The composition of claim 1, wherein the polysaccharides of green tea are contained in an amount of 0.1 to 20% by weight based on the total weight of the composition.

5. The composition of claim 1, wherein the cosmetic composition is used for skin whitening.

6. The composition of claim 1, wherein the cosmetic composition is used for skin whitening.

7. The composition of claim 1, wherein the cosmetic composition is used for skin moisturization.

8. The composition of claim 1, wherein the cosmetic composition is used for skin moisturization.

9. The composition of claim 1, wherein the cosmetic composition is used for improving skin wrinkle.

10. The composition of claim 1, wherein the cosmetic composition is used for improving skin wrinkle.

* * * * *